US006201984B1

(12) United States Patent
Funda et al.

(10) Patent No.: US 6,201,984 B1
(45) Date of Patent: *Mar. 13, 2001

(54) SYSTEM AND METHOD FOR AUGMENTATION OF ENDOSCOPIC SURGERY

(75) Inventors: Janez Funda, Valhalla; David Aruthur LaRose, Croton on Hudson; Russell Highsmith Taylor, Ossining, all of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/325,761

(22) Filed: Jan. 26, 1995

Related U.S. Application Data

(63) Continuation of application No. 07/889,215, filed on May 27, 1992, now Pat. No. 5,417,210, and a continuation-in-part of application No. 08/234,825, filed on Apr. 28, 1994, now Pat. No. 5,402,801, which is a division of application No. 08/147,008, filed on Nov. 21, 1993, now Pat. No. 5,976,156, which is a continuation of application No. 07/714,816, filed on Jun. 13, 1991, now abandoned.

(51) Int. Cl.[7] .................................................... A61B 5/05
(52) U.S. Cl. ........................................ 600/407; 606/130
(58) Field of Search ..................................... 600/424, 102, 600/117, 118, 109, 427, 407; 901/2, 3, 33, 34, 41, 44, 46; 606/130

(56) References Cited

U.S. PATENT DOCUMENTS

| | | |
|---|---|---|
| 4,058,001 | 11/1977 | Waxman . |
| 4,191,468 | 3/1980 | Scully ..................................... 356/17 |
| 4,456,961 | 6/1984 | Price et al. . |

(List continued on next page.)

FOREIGN PATENT DOCUMENTS

| | | |
|---|---|---|
| 3804491 | 6/1989 | (DE) . |
| 9216141 | 1/1992 | (WO) . |
| WO 95/01757 | 1/1995 | (WO) ............................ A61B/19/00 |

OTHER PUBLICATIONS

Adams et al., "Computer–Assisted Surgery," *IEEE Computer Graphics & Applications, Medical Imaging*, pp. 43–51, (May 1990).

Alexander, "Impacts of Telemation on Modern Society," *International Centre for Mechanical Sciences, First CISM—IFToMM Symposium on Robots and Manipulators*, vol. II, pp. 121–136 (Sep. 5–8, 1973).

Fisher, "Virtual Interface Environment," *IEEE/AIAA, 7th Digital Avionics Systems Conference*, Fort Worth, Texas, pp. 346–350, (Oct. 13–16, 1986).

(List continued on next page.)

*Primary Examiner*—Brian L. Casler
(74) *Attorney, Agent, or Firm*—Louis J. Percello

(57) ABSTRACT

The present method and apparatus use image processing to determine information about the position of a designated object. The invention is particularly useful in applications where the object is difficult to view or locate. In particular, the invention is used in endoscopic surgery to determine positional information about an anatomical feature within a patient's body. The positional information is then used to position or reposition an instrument (surgical instrument) in relation to the designated object (anatomical feature).

The invention comprises an instrument which is placed in relation to the designated object and which is capable of sending information about the object to a computer. Image processing methods are used to generated images of the object and determine positional information about it. This information can be used as input to robotic devices or can be rendered, in various ways (video graphics, speech synthesis), to a human user. Various input apparatus are attached to the transmitting or other used instruments to provide control inputs to the computer.

50 Claims, 8 Drawing Sheets

U.S. PATENT DOCUMENTS

| | | |
|---|---|---|
| 4,503,854 | 3/1985 | Jako . |
| 4,517,963 | 5/1985 | Michel . |
| 4,722,056 | 1/1988 | Roberts et al. . |
| 4,728,974 | 3/1988 | Nio et al. . |
| 4,833,383 | 5/1989 | Skarr et al. . |
| 4,854,301 | 8/1989 | Nakajima . |
| 4,863,133 | 9/1989 | Bonnell . |
| 4,891,767 | 1/1990 | Rzasa et al. . |
| 4,930,494 | 6/1990 | Takehama et al. . |
| 4,943,296 | 7/1990 | Funakubo et al. . |
| 4,945,914 | 8/1990 | Allen . |
| 4,989,253 | 1/1991 | Liang et al. . |
| 4,991,579 | 2/1991 | Allen . |
| 5,036,463 | 7/1991 | Abela et al. ............... 364/413.13 |
| 5,078,140 | 1/1992 | Kwoh ............................. 128/653.1 |
| 5,086,401 | 2/1992 | Glassman et al. . |
| 5,098,426 | 3/1992 | Sklar et al. ................. 364/413.13 |
| 5,184,601 | 2/1993 | Putman . |
| 5,188,111 * | 2/1993 | Yates et al. ........................ 604/281 |
| 5,196,688 | 3/1993 | Hesse et al. . |
| 5,216,596 | 6/1993 | Weinstein . |
| 5,236,432 | 8/1993 | Matsen, III et al. . |
| 5,251,127 | 10/1993 | Raab . |
| 5,261,404 | 11/1993 | Mick et al. ..................... 128/662.06 |
| 5,279,309 | 1/1994 | Taylor et al. . |
| 5,297,238 | 3/1994 | Wang et al. . |
| 5,321,353 | 6/1994 | Furness . |
| 5,339,799 | 8/1994 | Kami et al. . |
| 5,368,015 | 11/1994 | Wilk . |
| 5,398,685 | 3/1995 | Wilk et al. . |
| 5,402,801 * | 4/1995 | Taylor ................................. 128/898 |
| 5,417,210 | 5/1995 | Funda et al. . |
| 5,445,166 | 8/1995 | Taylor . |
| 5,494,034 * | 2/1996 | Schlondorff et al. ............... 606/130 |
| 5,515,478 | 5/1996 | Wang . |
| 5,572,999 * | 11/1996 | Funda et al. ........................ 600/407 |
| 5,848,967 * | 12/1998 | Cosman ............................. 600/426 |
| 5,907,664 * | 5/1999 | Wang et al. ......................... 606/19 |

OTHER PUBLICATIONS

Balogh et al., "Simulation and Error Analysis for a Stereotactic Pointing System," *IEEE Engineering in Medicine & Biology Society, 11th Annual International Conference*, vol. II: (Nov. 9–12, 1989) 11 page.

*Third World Congress of Endoscopic Surgery*, Bordeaux Jun. 18–20, 1992, Besant et al., "Camera Control for Laparoscopic Surgery by Speech–recognizing Robot: Constant Attention and Better Use of Personnel," Abstract No. 5, Session CL25/1, Krishnan et al., "Design Considerations of a New Generation Endoscope Using Robotics and Computer Vision Technology," Abstract No. 276, Session CL25/2, Melzer et al., "Concept and Experimental Application of a Surgical robotic System. The Steerable MIS Instrument," Abstract CL25/3, Melzer, et al., "A Pneumatic Controlled Sewing Device for Endoscopic Application the MIS Sewing Instrument MSI," Abstract No. 7, Session CL25/4, Green et al., "Telepresence: Advanced Teleoperator Technology for Minimally Invasive Surgery," Abstract No. 704, Session CL25/5, Satava, RM., "3–D Vision Technology Applied to Advanced Minimally Invasive Surgery Systems," Abstract No. 833, Session 15/3.

Charles et al., "Design of a Surgeon–Machine Interface for Teleoperated Microsurgery," *IEEE Engineering in Medicine & Biology Society, 11th Annual International Conference* vol. 11 (Nov. 9–12, 1989), pp. 883–884.

Corcoran, "Robot for the Operating Room," *New York Times*, Jul. 20, 1992, 2 pages.

Davies et al., "A Surgeon Robot for Prostatectomies," *IEEE 1991 Fifth International conference on Advanced Robotics* pp. 870–876.

Dolan et al., "A Robot in An Operating Room: A Bull in a China Shop?", *IEEE/Ninth Annual conference of the Engineering in Medicine and Biology Society*, pp. 1096–1097.

Finlay, "The United Kingdom Advanced Medical Robotics Initiative," *IEEE Engineering in Medicine & Biology Society, 11th Annual International Conference*, vol. 11, pp. 885–886 (Nov. 9–12, 1989).

Finlay et al., "Small is Beautiful" *Armstrong Projests, Ltd*, Beaconsfield HP9 2JL, England, pp. 13–15.

Finlay, "Results of a Feasibility Study Into Applications For Advanced Medical Robots," *Joint Coordinating Forum for the International Advanced Robotics Programme*, Ottawa Ontario, Canada, (Jun. 23–24, 1998), pp. 2.1–2.6.

Fu et al., "Robotics: Control, Sensing, Vision, and Intelligence," McGraw–Hill Book Company, Chapter 2, pp. 12–76 and Chapter 5, pp. 201–265, Copyright 1987.

Garbini et al., "Robotic Instrumentation in Total Knee Arthroplasty," *33rd Annual Meeting, Orthopeadic Research Society*, Jan. 19–22, 1987, San Francisco, California, p. 413.

Gayed et al., "An Advanced Control Micromanipulator For Surgical Applications," *Systems Science*, vol. 13, No. 1–2, pp. 123–134 (1987).

Kavoussi et al., "Telerobotic Assisted Laparoscopic Surgery: Initial Laboratory and Clinical Experience" *Urology* 44(1):15–19, (Jul. 1994).

Kwoh et al., A Robot With Improved Absolute Positioning Accuracy for CT Guided Stereotactic Brain Surgery, *IEEE Transactions on Biomedical Engineering*, vol. 35, No. 2, pp. 153–160 (Feb. 1988).

Lavallee, "A New System For Computer Assisted Neurosurgery," *IEEE Engineering in Medicine & Biology Society, 11th Annual International Conference*, vol. 11 (Nov. 9–12, 1989), pp. 926–927.

Ng et al., "Robotic Surgery," *IEEE Engineering in Medicine and Biology*, Mar. 1993, pp. 120–125.

Orenstein et al., "Robotics in Laparoscopy and Thorarcoscopy" *The London Clinic*, 20 Devonshire Place, London, W1N 2DH, pp. 17, 19, 21.

Paul et al., "Development of a Surgical Robot for Cementless Total Hip Arthroplasty," *Clinical Orthopaedics and Related Research*, No. 285, pp. 57–66 (Dec. 1992).

Regalbuto et al., "A Model–Based Graphics Interface For Controlling A Semi–Autonomous Mobile Robot," *IEEE Engineering in Medicine & Biology Society, 11th Annual International Conference*, vol. 11 (Nov. 9–12, 1989), pp. 910–911.

Richter et al., "Telesurgery may bridge future gaps" *Times Tribune*, Sunday, Jan. 24, 1988, pp. A1, A16.

Tachi, et al., "Tele–Existence Master Slave System For Remote Manipulation (II)," *29th IEEE Conference on Decision and Control*, Honolulu, Hawaii, Dec. 5–7, 1990, vol. 1 of 6, pp. 85–90.

Taylor et al., "Robotic Total Hip Replacement Surgery in Dogs," *IEEE Engineering in Medicine & Biology Society, 11th Annual International Conference*, vol. 11 (Nov. 9–12, 1989), pp. 887–889.

Tejima, et al., "A New Microsurgical Robot System for Corneal Transplantation," *Precision Machinery*, vol. 2, pp. 1–9 (1988).

Thring, "Robots and Telechirs: Manipulators with Memory; Remote Manipulators; Machine Limbs for the Handicapped," *Ellis Horwood Series in Engineering ScienceI,* Chapter 5, pp. 122–195; Chapter 8, pp. 236–278; Chapter 9, pp. 279 (1983).

Trevelyan et al., "Motion Control for a Sheep Shearing Robot," *Robotics Research, The First International Symposium,* Chapter 2, pp. 177–190 (1984).

Trinder et al., "A Close Range Digital Photogrammetry System" *SPIE* 1395:440–4447, (1990).

Young et al., Editor, "Another Pair of Hands for Surgeon?" Perspective p. 27, (1972).

H. Podbielska, "Endoscopic Profilometry", Optical Engineering, vol. 30 No. 12, pp. 1981–1985, Dec. 1991.

R.Y. Tsai, "A Versatile Camera Calibration Technique for High–Accuracy 3D Machine Vision Metrology Using . . . ", IEEE Journal of Robotics and Automation, pp. 323–344, 1987.

R.Y. Tsai and R.K. Lenz, "A New Technique for Fully Autonomous and Efficient 3D Robotics Hand–Eye Calibration", Proc. 4th Int. Symp. on Robotics Research, pp. 287–298, Santa Cruz, 1988.

W.E. Smith et al, "Correction of Distortion in Endoscope Images", IEEE Transactions on Medical Imaging, vol. 11, No. 1, Mar. 1992.

H.P. Moravec, "Obstacle Avoidance and Navigation in the Real World by a Seeing Robot Rover", PhD thesis, Stanford University, 1980.

B. Preising et al, "A literature review: robots in medicine", IEEE Engineering in Medicine & Biology, vol. 10, No. 2, Jun. 1991, pp. 13–22.

M. Bajura et al, "Merging Virtual Objects with the Real World: Seeing Ultrasound Imagery within the Patient" Computer Graphics, 26, Jul. 1992 pp. 203–210.

* cited by examiner

FIG. 7
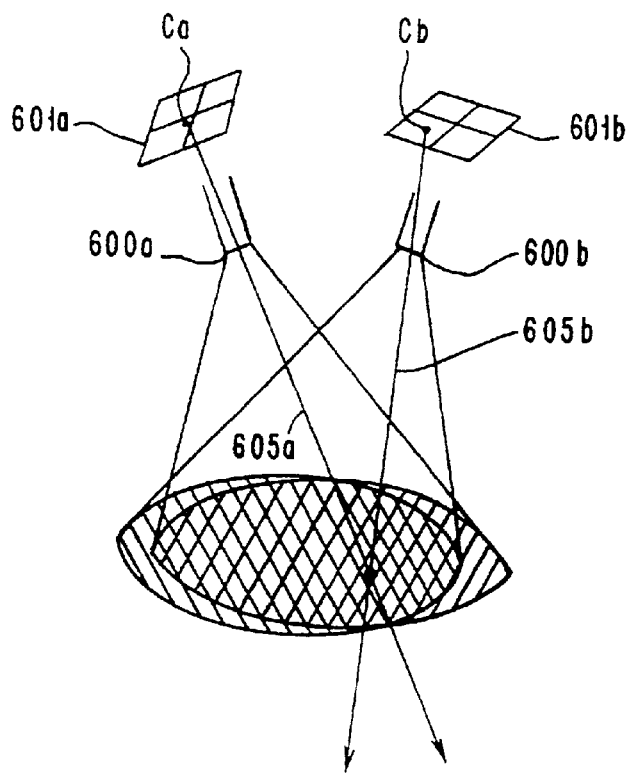
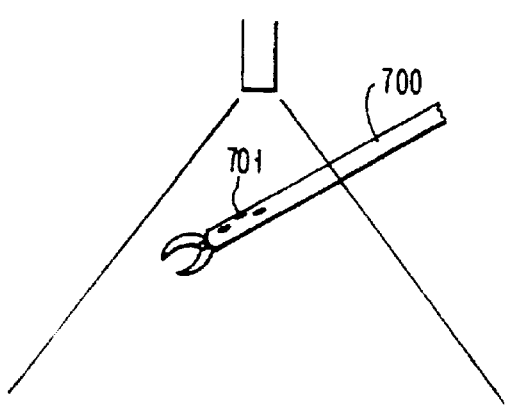
FIG. 8A
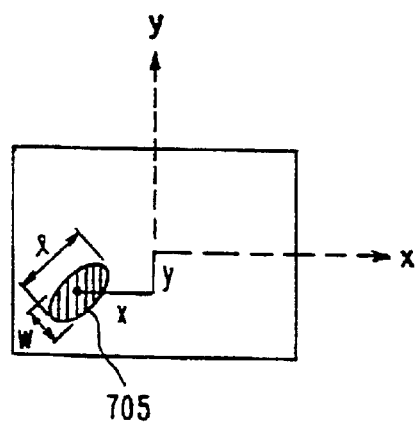
FIG. 8B

SYSTEM AND METHOD FOR AUGMENTATION OF ENDOSCOPIC SURGERY

This application is a continuation U.S. patent application Ser. No. 07/889,215, filed May 27, 1992 (U.S. Pat. No. 5,417,210), and is also a continuation-in-part of U.S. patent application Ser. No. 08/234,825, filed Apr. 28, 1994 (U.S. Pat. No. 5,402,801), which is a divisional of U.S. patent application Ser. No. 08/147,008, filed Nov. 21, 1993 (U.S. Pat. No. 5,976,156) which was a continuation of U.S. patent application Ser. No. 07/714,816, filed Jun. 13, 1991, now abandoned.

BACKGROUND OF THE INVENTION

1. Field of the Invention

This invention relates to the field of endoscopic surgery. More specifically the invention relates to obtaining accurate positional information about an anatomical structure within a patient's body and using this information to accurately position endoscopic cameras and surgical instruments within the patient's body.

2. Description of the Prior Art

Systems have been developed to augment a human surgeon's ability to perform surgery on a patient by providing the surgeon with intraoperative images of anatomical structures within the patient's body. Typically, these systems comprise a specialized form of camera or medical telescope. Further, a class of these systems, which includes endoscopic and laparoscopic instruments, has reduced the invasive nature of many surgical procedures.

This class of systems has two salient characteristics in common: First, the surgeon using the system cannot directly manipulate the patient's anatomy with his fingers, and second, the surgeon cannot directly observe what he is doing. Instead, the surgeon must rely on instruments that can be inserted through a trocar or through a working channel of an endoscope. Often, since his hands and attention are fully occupied in performing the procedure, the surgeon must rely on an assistant to point the endoscopic camera while the surgery is performed.

To ameliorate the awkwardness of this arrangement, robotic augmentation devices have been developed for endoscopic surgery. One such device is described in detail in a copending application entitled "System and Method for Augmentation of Surgery" Ser. No. 07/714,816 filed Jun. 13, 1991 which is herein incorporated by reference.

Robotic augmentation devices can potentially greatly assist surgeons during an operation. Robotic devices do not fatigue. Potentially, they can position medical telescopes and surgical instruments very accurately and can perform precise repositioning and repetitive functions. However, in order for these advantages to be realized, a number of problems need to be solved. The surgeon still needs to determine what motions the robotic device is to make and requires a means to communicate with the computer controlling the robot. In a few cases, such as orthopaedic machining of bone or preplanned excision of a tissue volume determined from preoperative medical images (such as CT or MRI scans), these motions may be preplanned. However, in other cases, the surgeon needs to directly observe the patient's anatomy and interactively specify the motions to be made relative to anatomical features and the medical telescopes. In these cases, means of accurately locating anatomical features and instruments relative to the medical telescopes and to each other and of using this information to control the robotic augmentation aids are necessary.

A specialized robotic device for stepping a resectoscope through a preprogrammed sequence of cuts in thranurethral prostatectomies has been developed. However, this system does not address the problem of providing the surgeon with a convenient means of controlling the view available through an endoscopic device or of providing the surgeon with means of interactively manipulating surgical instruments in response to intraoperative imaging and other sensory information.

There has been one attempt to provide voice control of a flexible endoscope in which servomotors attached directly to the control knobs of a commercial flexible endoscope were activated in response to voice commands by the surgeon. Difficulties of this approach include: (a) the surgeon (or an assistant) must still determine which direction to deflect the endoscope tip to provide a desired view and, consequently, must keep track of the relationship between the endoscope tip and the anatomical structures being observed; (b) these corrections must be made continually, distracting the surgeon from more important matters; and (c) the use of voice commands for this purpose is subject to errors, potentially distracting to the surgeon, and may make the use (if voice for communication between the surgeon and operating room personnel more difficult.

Several research efforts are directed to providing improved mechanisms for flexible endoscopes. These devices do not, however, simplify the surgeon's problem of controlling the endoscopic camera to obtain a desired view, either by himself or by communicating with a skilled operator.

3. Statement of Problems With the Prior Art

Unfortunately, the medical telescopes which are used in minimally invasive surgery have limited fields of view. As a result, only a small part of the anatomical feature hidden inside the patient's body can be viewed at a one time. Furthermore, surgical telescopes typically provide only a single vantage point at any one time and it is difficult to provide the desired view.

Normally, to compensate for this limited field of view, a surgical assistant operates the telescope, reorienting it to produce many views of the anatomical feature. While doing this, the assistant must continuously keep track of the relative orientation between the telescope and the patient's anatomy in order to be able to quickly and correctly aim the telescope at the surgeon's request. He or she must also correctly interpret the surgeon's desires, which are not always evident from the surgeon's verbal comments.

This creates a number of problems. Surgical procedures of this nature now require an additional highly-skilled person to assist the surgeon in manipulating the medical telescope because the surgeon is using both of his hands performing other tasks. The communication that is required between the surgeon and the assistant increases the potential for an error while performing the surgery. The surgeon (and assistant) have to develop and keep a mental image of the entire hidden anatomical feature because the telescope can not capture the full image of the feature. Many telescopes, whether flexible or rigid, provide an oblique view, i.e., the direction of view is not coincident with the main axis of the telescope. This further exacerbates the difficulties of correctly aiming the telescope to achieve a desired view and increases the likelihood that the surgeon or the assistant could misconstrue the image presented or lose the orientation of the telescope with respect to the anatomical feature. Human fatigue contributes to a degradation of positioning of the telescope and/or of the interpretation of the images that the telescope transmits.

Accordingly, there is a need for a way to obtain accurate and reliable information about the position and appearance of anatomical features hidden within a body. There also is a need for an apparatus to accurately position and orient surgical instruments and/or medical telescopes within a body and to provide accurate information about their position with respect to hidden anatomical features. Further, there is a need to provide a reliable and accurate interface between the surgeon and his surgical instruments so that he can accurately position these instruments with respect to an anatomical feature within a body without removing his hands from his instruments.

OBJECTIVES

An objective of this invention is to provide an improved method to obtain and display accurate information about the position of an anatomical feature within a patient's body.

Also an objective of this invention is to provide an improved method of positioning endoscopic cameras and other surgical instruments within a patient's body.

A further objective of this invention is to provide an interface for a surgeon to accurately position an endoscopic camera and/or other surgical instruments within a patient's body without removing his hands from the instrument.

BRIEF DESCRIPTION OF THE DRAWINGS

FIG. 7 shows a method of computing a position in three dimensions using two nonparallel camera vantage points.

FIG. 8 shows the use of passive visual targets to determine a position of a surgical instrument.

SUMMARY OF THE INVENTION

The present invention is a method and apparatus for determining positional information about an object and then using this information to position instruments in relation to the object. The invention has many applications but is particularly useful when the object is hidden from view or in a location that is difficult to access. One preferred embodiment, used in endoscopic surgery, determines positional information about a designated anatomical feature which is hidden within a patient's body. The information is used to position surgical instruments in the body with respect to the anatomical feature.

The invention first positions an instrument, e.g. a surgical instrument inserted inside a patient's body, at a desired position relative to a designated object (anatomical feature). The instrument is capable of transmitting an image of the object to a computer which then determines positional information about the object by using various types of image processing. The information is then related to a human (e.g., a surgeon) or to a computer controlling a robotic apparatus. The positional information is used to position or reposition the transmitting instrument and/or other instruments relative to the designated object.

To further facilitate use of the invention, a number of different output modes for conveying information from the imaging instruments and computer to humans in the operating room are provided.

To further facilitate use of the invention, input devices are incorporated on the inserted instruments so that a human user can input requests to the system while concurrently manipulating the instrument. Other methods of inputting requests to the system, such as voice recognition systems, are also incorporated so that communications with the system does not interfere with instrument manipulation.

DETAILED DESCRIPTION OF THE INVENTION

Figure 1:
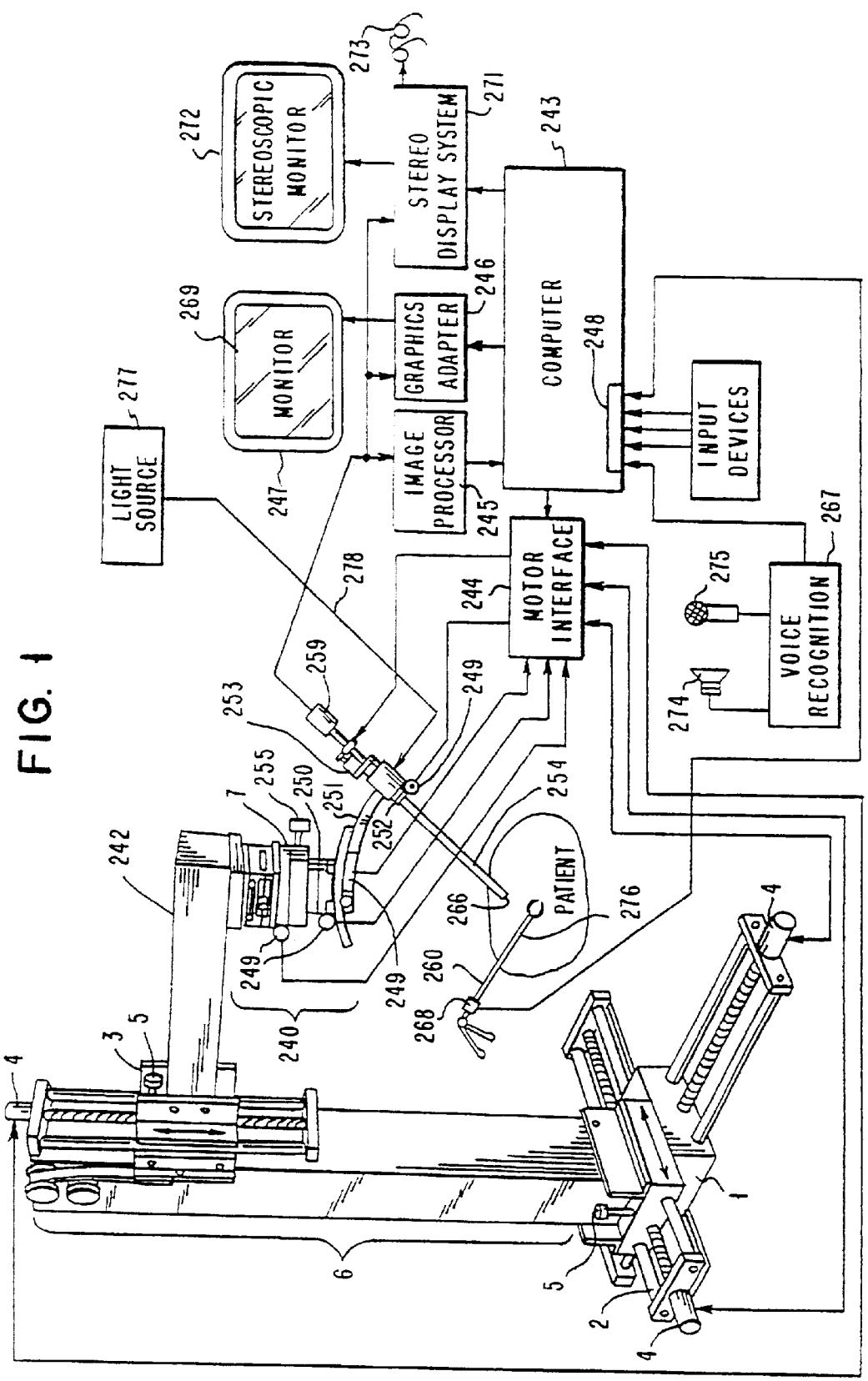
FIG. 1 shows a schematic view of a system used for computer augmentation of surgical procedures.

Referring to FIG. 1, there is shown a schematic view of a system for use in computer augmentation of laparoscopic or similar procedures. The system generally comprises a manipulator apparatus or robot 242, a computer 243, a drive motor interface 244, a monoscopic monitor 247 with a suitable image processor 245 and graphics adaptor 246, a stereoscopic monitor 272 with suitable stereo display system 271, and a terminal 248 for connecting additional input devices to computer 243.

A manipulator similar to the manipulator 242, used in this preferred embodiment, is described in detail in the copending U.S. application Ser. No. 07/714,816 filed on Jun. 13, 1991.

Figure 2:
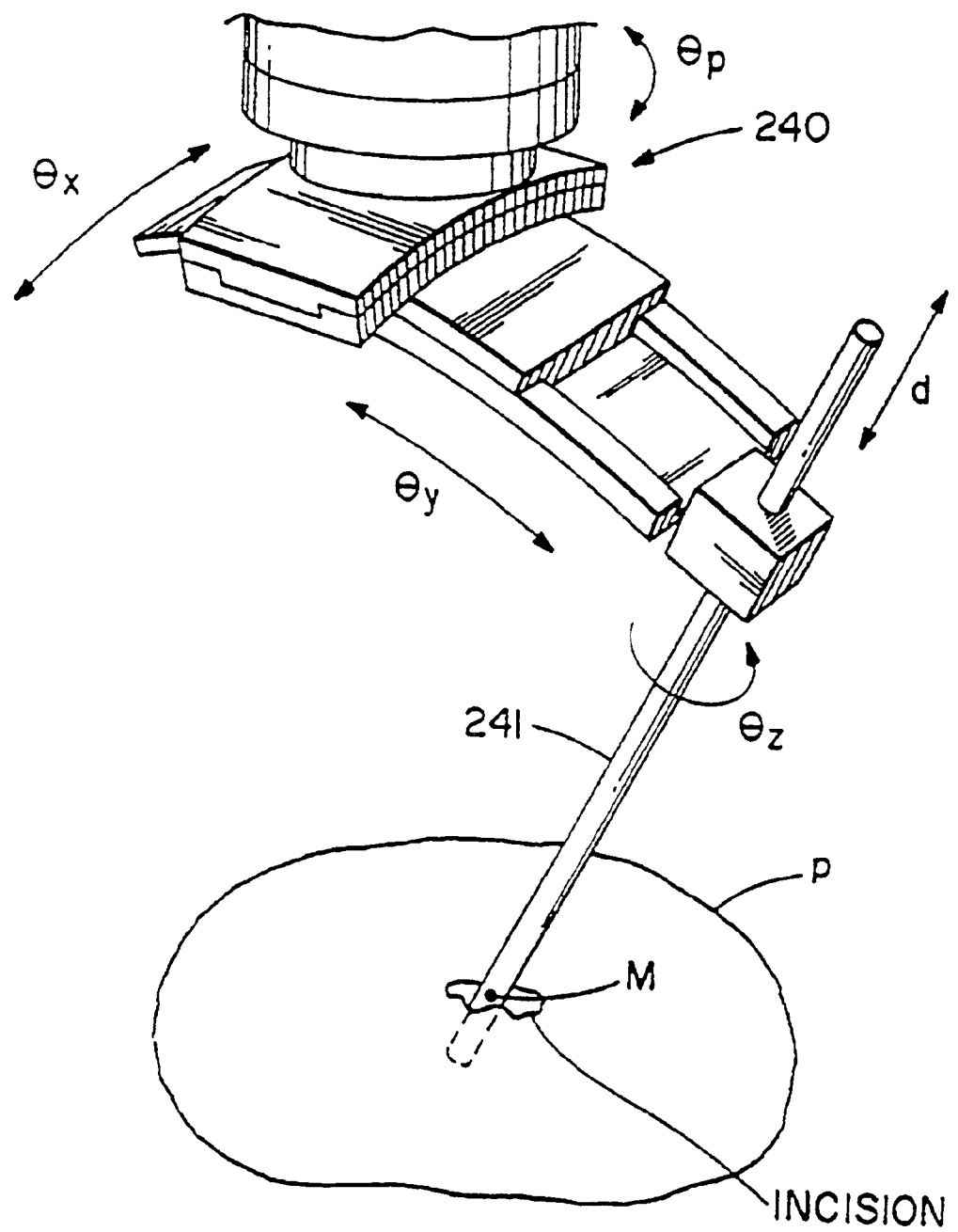
FIG. 2 is a detail of FIG. 1 showing a distal fine motion rotational manipulator.

Referring to FIGS. 1 and 2, the manipulator 242 comprises a proximal rectilinear manipulator 6 and a remote center-of-motion distal manipulator 240. The proximal manipulator 6 comprises three mutually orthogonal sliding motion sections 1, 2, and 3, which provide motion in the X, Y, and Z directions. Sections 1, 2, and 3 are equipped with computer-controlled motorized drives 4 connected to motion interface 244 and also have manual locking clamps 5. The remote center-of-motion distal manipulator 240 comprises rotational sections 7, 250, 251, and 252 to provide $\theta_p$, $\theta_x$, $\theta_y$, and distal $\theta_z$ rotational motion, and a slide motor 253 adapted to axially slide instrument 254. These sections are equipped with computer-controlled motorized drives 249 interfaced to motor interface 244 and have manual locking clamps 255. Each of the moving sections of manipulator 242 can be actuated either manually or under computer control and can optionally be locked by a manual locking device. All the motorized drives 4 and 249 are controlled by computer 243 through motor interface 244.

Referring to FIG. 2, there is shown a schematic view of the distal fine motion rotational manipulator 240 with an instrument 241 inserted through an incision into a patient's body. In the embodiment shown, the distal manipulator 240 provides a five degree-of-freedom ($\theta_p$, $\theta_x$, $\theta_y$, $\theta_z$, and d) remote center-of-motion wrist, which is supported by the aforementioned proximal positioning system with three orthogonal linear degrees of freedom (X, Y, and Z). The proximal linear degrees of freedom are used to place the center-of-motion M of the remote center-of-motion wrist at the position of insertion into the patient's body P. Any alternative mechanical structure (such as a SCARA manipulator, manufactured and sold by IBM) with sufficient degrees of freedom could be substituted for this purpose.

The four distal revolute degrees of freedom and the sliding degree of freedom of manipulator 240 give the surgeon a five degree-of-freedom spherical work volume centered at the insertion point M. These degrees of freedom may be selectively locked or moved independently (manually or under computer control) to assist the surgeon in achieving a desired precise alignment. Furthermore, small motions within the work volume can be achieved with only small motions of the individual axes. The point M (i.e., the point at which the surgical instrument enters the patient) remains unaffected by any motions of the distal manipulator 240. Thus the manipulator may be moved through its work volume without requiring that the patient position be moved or that the size of the entry wound be enlarged.

One consequence of this design is that motion of the proximal manipulator 6 is not needed unless the patient is moved. Consequently, in a preferred embodiment, the motion of proximal manipulator 6 is disabled by manual locking and/or disabling of drive motors whenever an instrument is inserted into the patient. In this mode, the control computer 243 interprets commands requesting motion of manipulator 242 as follows. When a motion is requested, the control computer 243 attempts to satisfy the request by moving only distal manipulator 240. If the motion can be accomplished in more than one way, the computer selects the motion that minimizes the motion of the most proximal revolute motion section 7 (i.e., it minimizes motion of $\theta_p$). If the motion cannot be accomplished perfectly, the computer selects the motion of distal manipulator 240 that most closely approximates the desired motion. Modes are available to select minimization of positional error of the tip of instrument 241, orientation error, or weighted combinations thereof. If the error is greater than a prespecified threshold amount, the control computer notifies the surgeon using synthesized speech, an audible alarm, or other means, and makes no motion unless the surgeon explicitly instructs it to proceed, using voice recognition or other input modality. One alternative embodiment might seek always to minimize the total motion of the distal manipulator 240, again forbidding motion of proximal manipulator 6 whenever a surgical instrument held by the distal manipulator is inserted into the patient's body. Yet another might permit small motions of the proximal manipulator, so long as the center-of-motion M stays within a specified threshold distance (e.g., 3 mm) of the original value.

If desired, a flexible tip may be added to the distal end of instrument 241 to provide additional degrees of freedom. In the case where a viewing instrument such as instrument 254 is used, an additional degree-of-freedom in adjusting the gaze direction may be provided by adding an adjustable-angle mirror or prism to the distal end of the instrument.

Referring again to FIG. 1, the instrument 254, in the embodiment shown, includes a video camera 259 and a light source 277 connected to the instrument via a fiberoptic cable 278. The video output of the camera 259 is fed into the graphics adaptor 246, where it may be optionally mixed with graphics output from computer 243 and displayed on monitor 247. The video output from the camera is also optionally fed into the image processing system 245, which analyzes the image produced by the camera and provides information to computer 243 about the relative position of the surgeon's instruments, the camera, and the patient's anatomy. The video information from the camera may be also optionally supplied to the stereo display system 271, which can assemble a stereoscopic view of the patient's anatomy from two or more images taken from different vantage points and display the image on the stereoscopic monitor 272.

In one preferred embodiment, the stereo display system is a StereoGraphics CrystalEyes (trademark of StereoGraphics, Inc.) system, where the two video signals are displayed on a stereoscopic monitor which alternatively displays the left and right eye image at a frequency of 120 Hz, updating the video information for each eye 60 times per second. The surgeon wears stereoscopic liquid crystal (LC) goggles 273, which are synchronized with the monitor and alternatively block light from entering left and right eye such that the left eye receives only the video signal from the left camera and the right eye receives only the information from the right camera. The frequency of alternation between left and right images is sufficiently high such that the surgeon perceives no flicker but rather a continuous stereoscopic image of the patient's anatomy. Other stereo display technologies are available and may be used.

In the embodiment shown, the surgeon is using a second surgical instrument 260 inside the patient's body, which has passive visual targets 276 placed on it. These targets 276 are markings on the instrument and are chosen so as to be easily locatable by the image processing system 245 in the images supplied by the camera 259.

The set of input/output devices attached to input/output interface 248 of computer 243 shown in FIG. 1 may include a computer voice recognition and synthesis system 267, a joystick 268 mounted on the surgical instrument 260 and a sterilized touch screen 269 mounted on monitor 247. In the preferred embodiment the joystick is a small device, functionally identical to a 2D or 3D mouse, but designed such that it can be mounted directly onto a surgical instrument and such that at least two degrees of freedom of motion can be specified by applying pressure on a small joystick protruding from the device. One implementation of such a device uses strain gauges to translate an applied pressure or force into incremental displacement or velocity information. In another embodiment, a six degree-of-freedom input device, such as Spaceball (A Trademark owned by Spaceball Technologies, Inc.) could be used used to specify motion in any of the six degrees of freedom. Such a device could be mounted on a surgical instrument, on the manipulator structure, or at any other convenient point. One advantage of mounting an input device such as a small joystick on a surgical instrument is that the surgeon can easily manipulate the joystick without removing his hands from the surgical instrument, thus permitting him to provide information to the computer (for example, of a desired direction of motion of a medical telescope) without interrupting his work.

The speech recognition and synthesis system 267 includes means of inputting information to the system, such as a (possibly head mounted) microphone 275, and a means of conveying information to the surgeon, such as a speaker 274. The speech recognition system 267 is capable of understanding a vocabulary of instructions spoken by the surgeon and can relate the information about the commands it has received to the computer 243. The surgeon may use any of these modalities, either separately or in combination, to position graphic objects on the monitor 247, to select commands or operating modes from menus, and to command motions of the manipulator 242.

Figure 3:
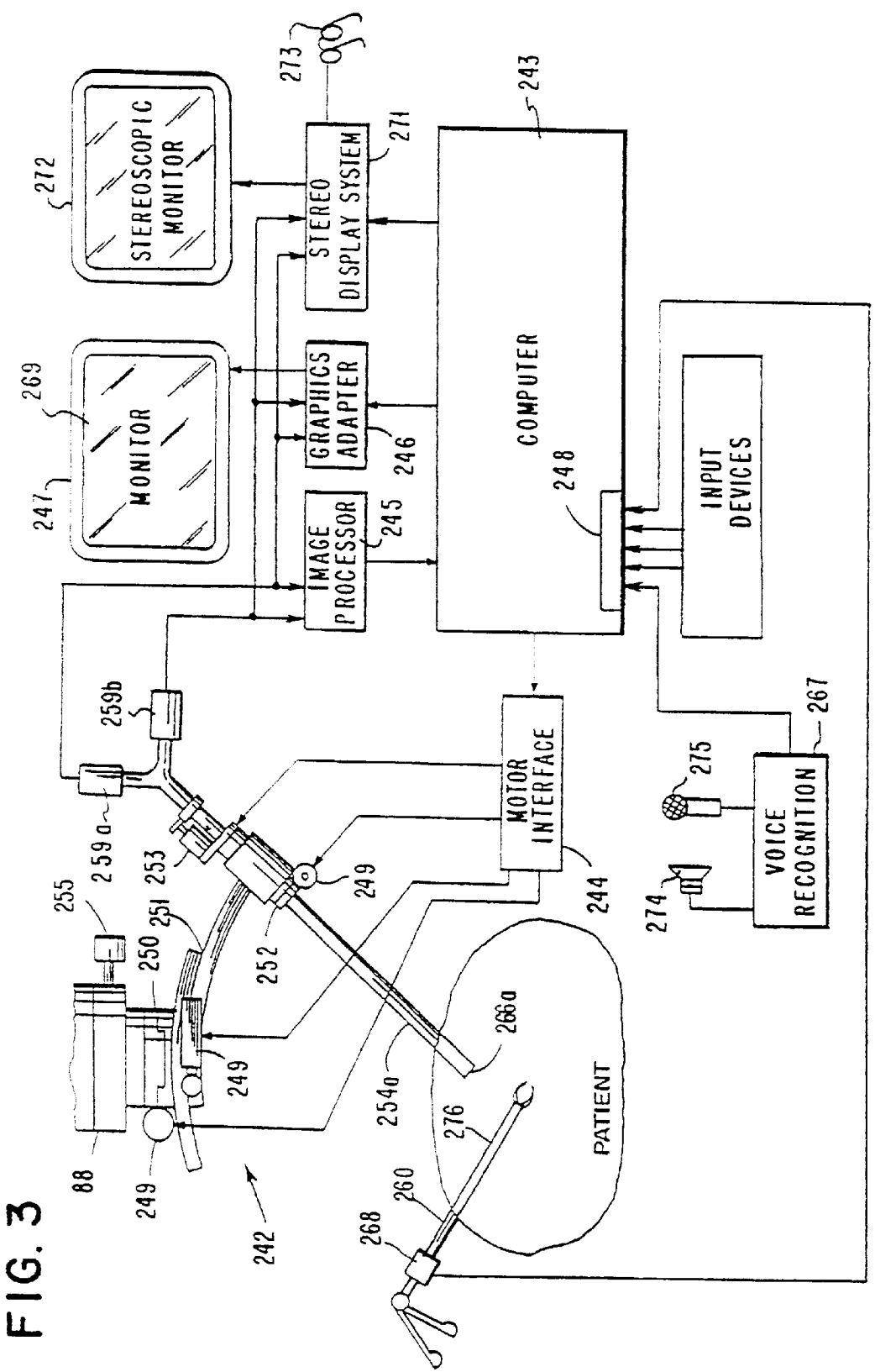
FIG. 3 shows an embodiment of the invention using a stereoscopic visualization system.

Referring to FIG. 3, there is shown an alternative embodiment of the system for computer augmentation of laparoscopic or similar surgical procedures. In this embodiment, the surgical instrument 254a is a stereoscopic medical camera, which incorporates two independent lens systems or optical fibers and is capable of transmitting two simultaneous images from the patient's body. The two lenses are separated by a small (known) distance and are thus able to provide a stereoscopic image. One embodiment of such a device would comprise two side-by-side fiberoptic bundles or lens systems and one fiberoptic light channel. The assembly would be surrounded by a suitable cylindrical casing. The video signals from the two cameras 259a and 259b are fed into the stereo display system 271 and displayed to the surgeon on a stereoscopic display monitor 272. Using interface hardware known in the art, both video signals are also optionally supplied to the image processing system 245 and the graphics adapter 246.

Figure 4:
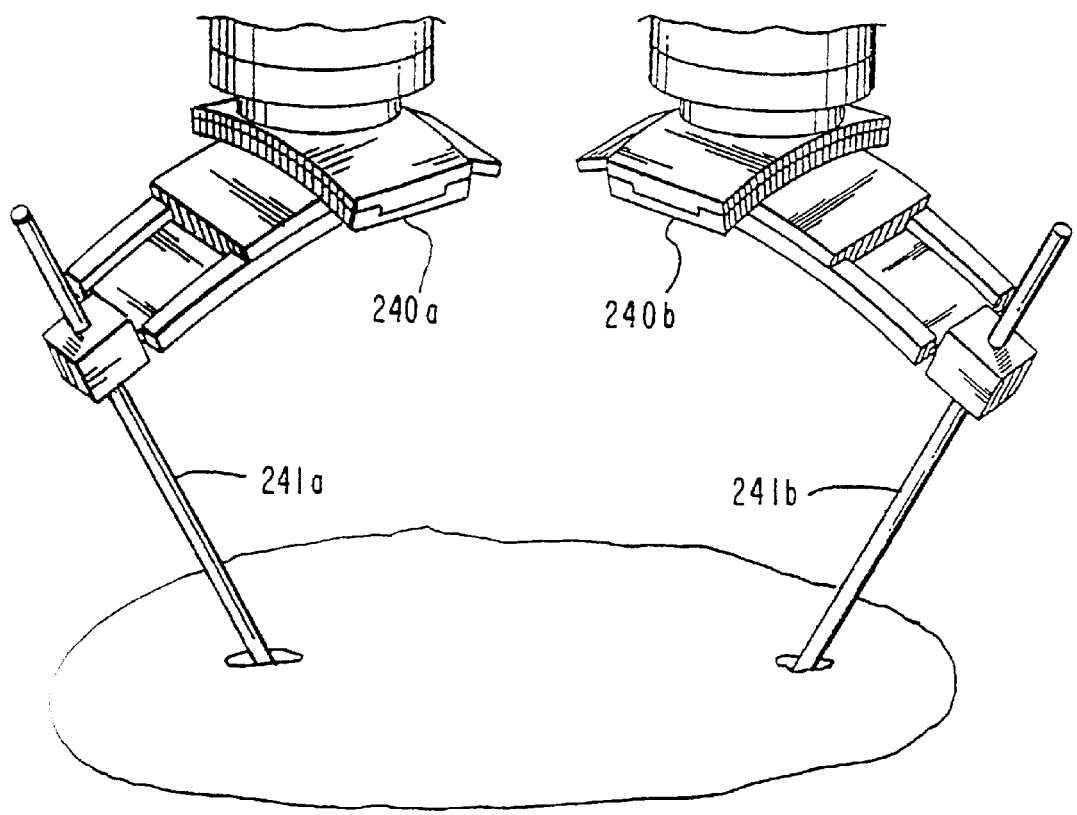
FIG. 4 shows an embodiment of the present invention comprising two robotic manipulators.

Another embodiment of the system is shown in FIG. 4, where the system comprises two manipulators 240a and 240b, carrying surgical instruments 241a and 241b, respectively. In one embodiment, one of the surgical instruments is a medical telescope, whereas the other instrument is a surgical tool, such as medical forceps. Since both instruments are attached to robotic devices, both can be actively positioned under computer control. On the other hand, as with the single manipulator arm in the case above, either or both robots can be controlled manually by releasing, adjusting, and relocking joint axes one at a time. In an alternative embodiment, both surgical instruments 241a and 241b comprise medical telescopes or other means of transmitting an image outside of a patient's body. In such an embodiment, one of the instruments (for example, 241a) may also comprise a surgical tool such as a miniaturized surgical forceps. In this case, information from images taken at two vantage points may be combined to provide precise 3D information to assist in placing the surgical instrument precisely on the desired portion of the patient's anatomy.

Referring again to FIG. 1, the image processing system 245 may be used to locate features on the patients anatomy of interest to the surgeon. In this mode, the surgeon would designate a feature of interest by any of a number of means to be explained below. On the surgeon's command, supplied via any appropriate input device attached to the terminal 248, the computer 243 would instruct the image processing system 245 to acquire an image and precisely locate the designated anatomical feature. In one embodiment, a reference image of the designated feature would be acquired in response to the surgeon's command and stored. Image correlation techniques would be used to locate the feature during surgery. In an alternative embodiment, synthetic reference images could be generated from computer reconstructions of preoperative medical images and models. Once a feature has been located, the manipulator 242 can be moved to place the feature at any desired position in the camera field of view. If desired, an additional image may be acquired, the feature re-located, and a further adjustment made to refine the desired placement of the camera. This process may be repeated a number of times to "zero in" on a feature to any desired accuracy. Each of the foregoing steps is explained below.

Figure 5:
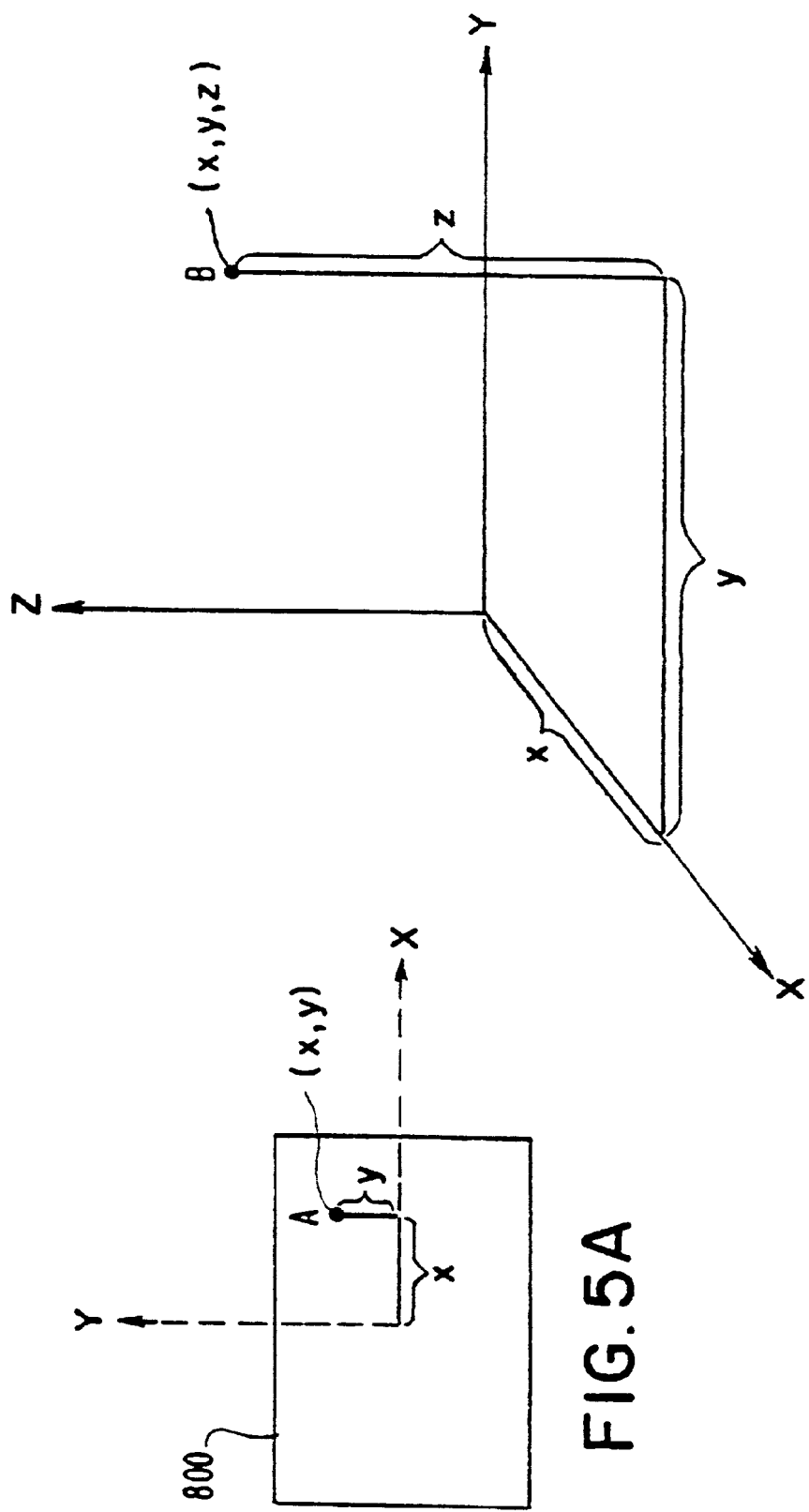
FIG. 5 shows positions in 2D and 3D Cartesian coordinate systems.

As a matter of nomenclature, we will in the following text refer to positional information in a number of ways. Unless otherwise specified, the terms "position" and "location" will be used interchangeably. We will be referring to two-dimensional (2D) and three-dimensional (3D) positions. When referring to an image obtained by a single monoscopic camera, an "image location" or "image position" should be understood as a 2D location within the 2D image. Referring to FIG. 5a, such a location A (within a 2D image 800) is given as a pair of coordinates (x,y,z). When the image is stereoscopic, "image location" or "image position" should be understood as a 3D location within the volume of the stereoscopic image. Referring to FIG. 5b, such a location B is described by a triple of coordinates (x,y,z). We will also refer to positions of anatomical features. Such features are part of the patient's anatomy and all references to "feature location" or "feature position" should be understood as 3D positional information about the feature in question.

In order to use and manipulate images of the patient's anatomy, images must first be acquired. Referring to FIG. 1, this is done by feeding the live video signal from camera 259 into the image processing system 245 comprising at least one video digitizer. A video digitizer is a device capable of converting an analog video signal into a digital signal, which can be stored in computer memory and arbitrarily modified by the computer. Conversely, a video digitizer can also convert a digitized (and possibly modified) video signal back into analog form for display on a standard monitor.

If positional information is to be extracted from images obtained by a camera/lens system, a mathematical model of the camera and the lens must be available to relate image points (i.e., points on the camera's imaging plane) to the corresponding world points (i.e., 3D locations in the actual environment). To a good approximation, a perfect camera/lens system can be modeled as a pin-hole system, illustrated in FIG. 6. The figure depicts a camera with a lens 600 positioned a distance f in front of the image plane 601. The quantity f is referred to as the focal length of the lens. A point $W=(x,y,z)$ lying in the plane 602 a distance $d=-z$ in front of the lens is imaged onto the image plane 601 at the location $C=(x',y')$, where $x|d=x'|f$ and $y|d=y'|f$.

Given the image coordinates (x',y') of a world point, the above relationships constitute two equations in three unknowns (x, y, and z) and are thus not sufficient to recover the 3D coordinates of the corresponding world point, W. Referring to FIG. 7, the information obtained from a single image 601a from a first vantage point 600a defines a ray 605a in 3D space originating at the image point $C_a$, passing through the lens center 600a, and extending to infinity. By definition, the actual world point W lies somewhere on this ray, but additional information is needed to determine its exact location. If a second image 601b, taken from a second vantage point 600b (whose position and orientation with respect to the first vantage point is known), is available, then the corresponding image point $C_b$ in the second image and the location of the second vantage point 600b define a second ray 605b in space, such that the world point W lies on this ray a well. Using known mathematical techniques, the two rays can be resolved in the same coordinate system and their intersection can be computed, giving the 3D world coordinates (x,y,z) of the point W.

Most camera lenses introduce distortions which causes the correspondence of world and image points to depart from the above pin-hole model. The process of calibrating the camera/lens system can estimate the nature and amount of such distortions and the resulting mathematical model can be used to effectively "undistort" the image points. The pin-hole camera model can then be applied to the undistorted image. A number of techniques for calibrating camera/lens systems are known.

As part of the interaction with a two-dimensional image of the patient's anatomy displayed to the surgeon on a conventional monitor, the surgeon may wish to designate (i.e., point to) a particular image location within the displayed image. The surgeon may point to a particular image location by using any of the following means: (a) by positioning a surgical instrument equipped with a distinct and clearly visible visual target so that the image of the visual target on the display coincides with the desired image location, (b) by manipulating a graphical object on the screen using an input device mounted on a surgical instrument (such as joystick 268 in FIGS. 1 and 3 or a similar device), or (c) by manipulating a graphical object on the screen using a conventional mouse. In method (a) the visual target may consist of a brightly colored spot or a known geometric pattern of such spots at a known position on the instrument (e.g., pattern 276 in FIGS. 1 and 3). The use of a bright color, distinct from any color naturally occurring inside the patient's body, greatly simplifies the problem of locating artificial visual targets and lessens the chances of erroneous location of such targets. Such spots on the surgical instrument can be located using known image processing techniques, involving thresholding (to isolate the spots from the rest of the image) and computationally determining the centers of the so obtained thresholded regions. In methods (b) and (c) the position of the feature of interest is taken as the final position of the graphical object.

Once the 2D coordinates of an image location have been specified to computer 243, the computer can confirm the location by marking the location with a graphical object superimposed on the image. In one embodiment of this method of confirming an image location to the surgeon, 2D cross-hair cursors or 2D box cursors can be used to show the location of interest in the image. The "image", in this context, can be either a TV camera image or a computer generated graphical rendition of the anatomical area of interest.

We have so far described a variety of methods for the surgeon to specify a particular 2D location of interest in a monoscopic image. We next discuss methods, such as image processing, to determine positional information about three-dimensional anatomical features and/or surgical instruments in the patient's body.

Referring to FIGS. 1 and 3, if a stereoscopic display (live or static) of the patient's anatomy is available during the surgical procedure, then a surgeon can designate the desired 3D anatomical feature of interest by manipulating a 3D stereoscopic graphical object (cursor) on the stereoscopic display 272 until the graphical object is coincident with the desired anatomical feature. Any of the appropriate aforementioned input devices and modalities 248 (such as the surgical tool mounted joystick or trackball, voice, etc.) can be used to specify the desired motion of the graphical object within the stereoscopic volume of the image.

If the actual physical size of a designated object is known, its distance from the viewing instrument may be estimated from the size of its image, as seen by the viewing instrument. Since we know that the feature lies on a ray originating at the center of image of the feature and passing through the vantage point as shown in FIG. 7, the position of the feature relative to the viewing instrument may then be computed. Let the size of the feature in the image be l, let the corresponding actual size of the feature be s, and let f denote the focal length of the camera. The distance z from the camera lens to the feature of interest can then be computed as z=(f×s)|l.

Referring to FIG. 8, in one embodiment, where passive visual targets 701 on a surgical instrument 700 are used, the position of a 3D feature (e.g., a surgical instrument 700) can be determined as follows: At least three non collinear circular spots 701 of known diameter s are marked on the surgical instrument 700 (FIG. 8a). Since the surgical instrument may have an arbitrary orientation with respect to the camera, these spots will in general appear on the image plane as ellipses 705 (FIG. 8b). However, the length of the major axis of each ellipse l will be the same as the diameter of the circular image that would be seen if the corresponding circular spot were presented at that same distance from the lens in such a manner that the plane in which it lies is perpendicular to the view axis of the camera. Let the length of the major axis of the observed ellipse as it appears in the image be l (FIG. 8b). Then the distance of the spot from the camera lens can be computed from z =(f×s)|l. Having performed this computation for at least three spots and knowing the position of the spot pattern with respect to the tip of the surgical instrument suffices to compute the 3D location of the tip of the surgical instrument with respect to the camera. Other techniques, known in the art, permit calculation of the position and orientation, relative to the camera, of a pattern of five dots from the 2D positions of their centroids in the image obtained. Other patterns of dots or other visual targets can be used as well. The 3D location of the tip of the instrument relative to the camera may then be readily computed from the known position of the tip relative to the visual target.

Figure 6:
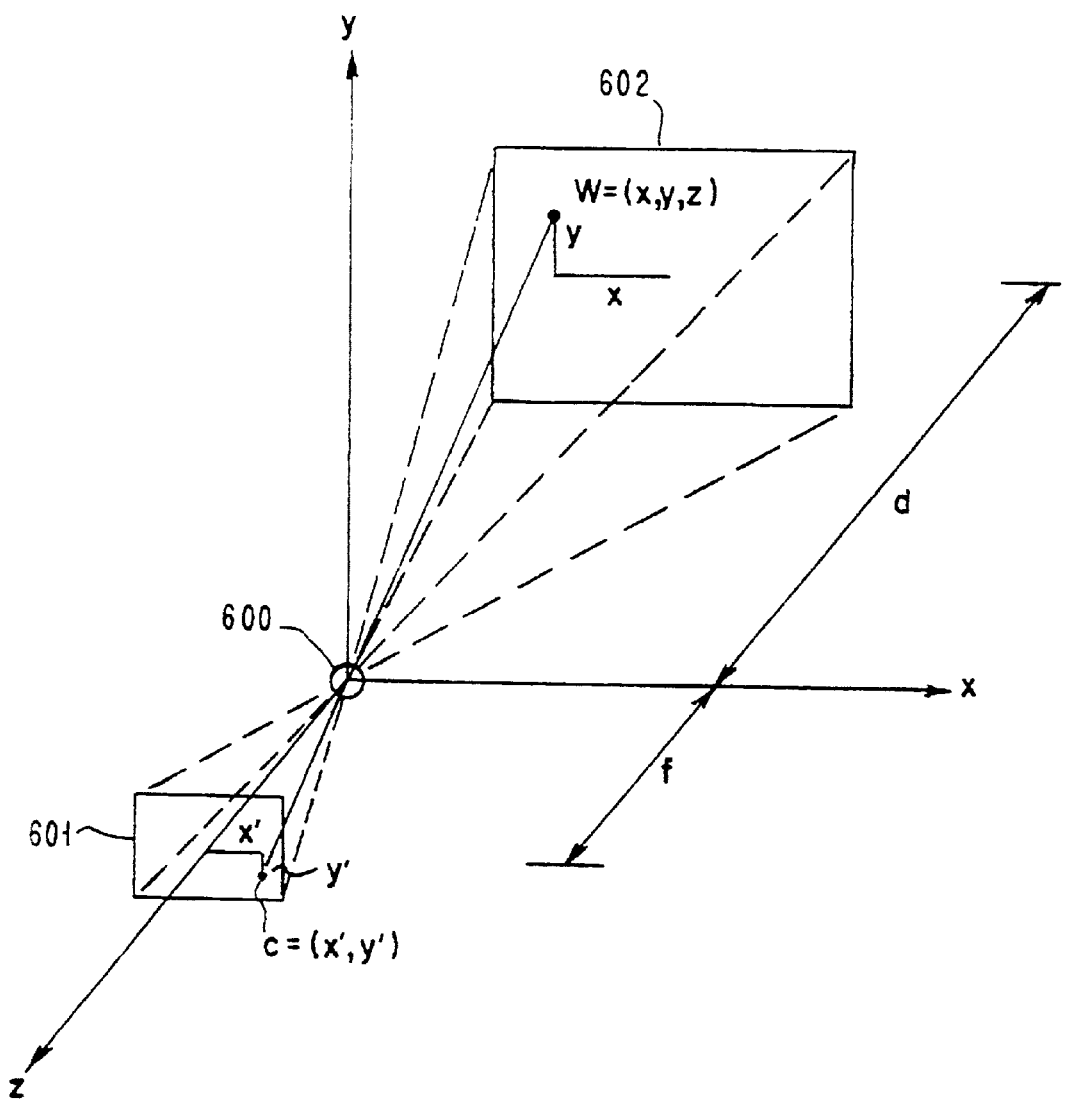
FIG. 6 shows the pin-hole mathematical model of a camera.
Figure 9:
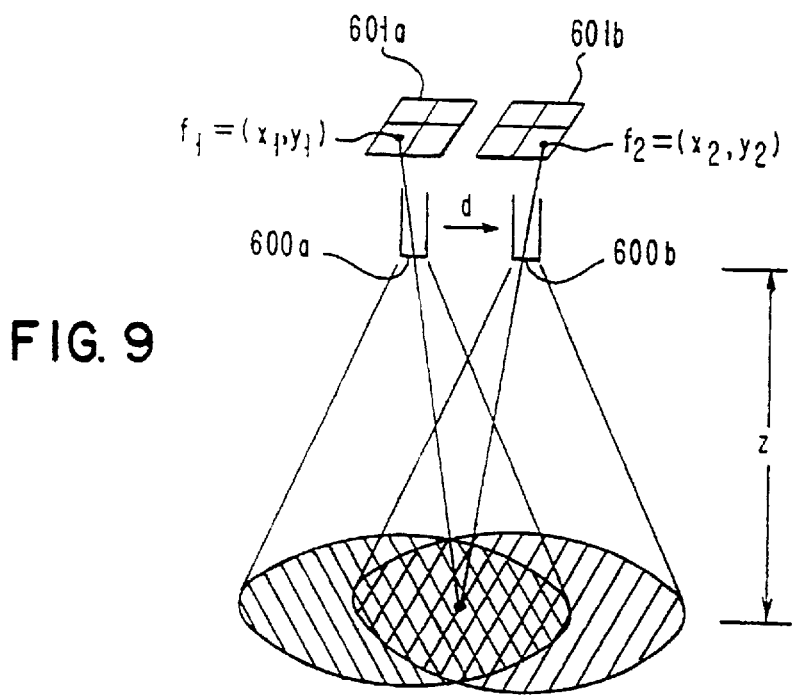
FIG. 9 shows a method of computing a position in three dimensions using two parallel camera vantage points.

Additionally, stereo image processing may be used to precisely locate 3D anatomical features. In one embodiment, image processing can be used in conjunction with a stereoscopic camera to locate an anatomical feature. Referring to FIG. 3, surgical instrument 254a is a stereoscopic medical camera, comprising of two independent lens systems or optical fibers and is capable of transmitting two simultaneous images from the patient's body. The lenses are separated by a small (known) distance d, as shown in FIG. 9. The 3D position of the anatomical feature relative to the camera tip can be computed from the pin-hole camera model (FIG. 6). Specifically, if the image plane locations of the center of the feature of interest in the two images are denoted by $f_1=(x_1,y_1)$ and $f_2=(x_2,y_2)$, as shown in FIG. 9, then the distance z of the feature center from the camera lens can be computed as z=(f×d)|c, where $$c = \sqrt{(x_2 - x_1)^2 + (y_2 - y_1)^2}$$

and f denotes the focal length of the camera. Image correlation techniques or other image processing techniques known to the art may be used to locate features in images.

Referring again to FIG. 9, in another embodiment, using only a monocular camera, image processing techniques can be used to determine the position of an anatomical feature in three dimensions as follows: A first image 601a of the anatomical feature is acquired and a reference representation (such as a multi-resolution image pyramid representation known in the image processing art) is stored. The manipulator 242 is used to displace the camera lens tip 600a laterally by a known amount d, and a second image 601b is acquired. The center of the feature of interest W is located in the second image, using the reference representation of the feature, by means of correlation techniques (such as multi-resolution normalized correlation methods known in the art) and the 3D displacement of the anatomical feature from the camera tip may be computed as in the case above. Specifically, if the image plane locations of the feature of interest W in the two images 601a and 601b are denoted by $f_1=(x_1,y_1)$ and $f_2=(x_2,y_2)$, respectively, then the distance z of the feature from the camera lens can be computed as z=(f×d)|c, where $$c = \sqrt{(x_2 - x_1)^2 + (y_2 - y_1)^2}$$

and f denotes the focal length of the camera.

In another embodiment, the physical constraint of maintaining minimal translational motion of the telescope with respect to the port of entry into the patient's body may preclude laterally displacing the telescope to obtain a second image, as described above. Referring to FIG. 7, in this embodiment, a first image 601a is obtained from the first vantage point and the center W of the feature of interest is located in the image at image location $C_a$. The telescope is then rotated by a small (known) amount about the port of entry, such that the desired feature is still within the field of view of the telescope, and a second image 601b is obtained. Note that the second vantage point has a different position and orientation than the first vantage point. The feature center W is located in the second image at image location $C_b$. The 3D position of the feature center W is then obtained by computing the intersection of the rays 605a and 605b, as described previously. As above, image correlation techniques or other image processing techniques known to the art may be used to locate features in images. Alternatively, the surgeon may be asked to manually designate the image location of the feature center in the two images using any of the means of designating image locations described previously.

Once a 3D feature has been designated and its 3D location successfully computed, computer 243 can confirm its location by marking the location with a 3D stereoscopic graphical object superimposed on the stereoscopic image of the area of interest. In one embodiment of this method of confirming 3D feature location to the surgeon, 3D cross-hair cursors or 3D box cursors can be used to show the feature's 3D location within the stereoscopic view volume. The "image", in this context, can be either a TV camera image or a computer generated graphical rendition of the anatomical area of interest.

Once the 3D positions of anatomical features are stored in computer 243, this information may be used to control the position and orientation of the camera tip relative to the features so as to provide any desired field of view.

Referring to FIG. 1, in one mode the surgeon can designate a first and a second 2D location in the image, using any of the means for designating 2D locations discussed above. The surgeon can then instruct the manipulator 242 (using any appropriate input device or modality as described earlier) to reposition the camera tip 266 so that the anatomical feature $f_1$, whose image appeared at the first 2D image location prior to camera motion, appears at the second 2D location in the image after the camera motion. The distance of the camera tip 266 from the anatomical feature $f_1$ remains constant during the camera motion. A special case of this mode is the case where the second 2D location is the center of the image. In this case the camera is repositioned so that the anatomical feature $f_1$ appears to move to the center of the displayed image, i.e., the camera is "centered" over the anatomical feature.

In another mode the surgeon can specify a sequence of 2D locations in an image and instruct the manipulator 242 to move the camera tip 266, at a constant elevation, so that the camera traverses the path defined by the sequence of 2D locations in the image. In one embodiment, this sequence of image locations can correspond to image locations of distinct small anatomical features within the camera's field of view. In another embodiment, the sequence of image locations can correspond to image locations of a boundary of a large anatomical feature, such as a blood vessel. This mode of repositioning the camera can be viewed also as specifying the desired apparent motion of an anatomical feature (corresponding to the last 2D location in the specified sequence) with respect to the image. The term "apparent motion of an anatomical feature" is used to emphasize that the anatomical feature does not physically move, but only appears to move relative to the image due to the motion of the camera. Specifically, the execution of this mode proceeds as follows: The sequence of 2D image locations is processed by computer 243 into a continuous path by the process of interpolation. The camera is then centered over the anatomical feature corresponding to the first designated 2D image location as described in the previous paragraph. The camera is then repeatedly positioned so as to center each of the successive interpolated 2D locations within its field of view, thereby effectively traversing the path as defined by the surgeon. The surgeon directly controls both the direction and speed of the camera motion by means of the surgical tool mounted joystick or any other appropriate input means.

In another mode the surgeon can specify an increment of motion along the camera's axis of view and reposition the camera along this axis by the designated amount. The "axis of view" in this context is defined as the line joining the camera lens center and the point p on the patient's anatomy which appears in the center of the camera image. This mode effectively implements, a zoom function with respect to a 3D anatomical feature, where the zoom factor (i.e., desired enlargement or contraction of the image of the anatomical feature) is specified by the surgeon interactively. In particular, this mode can be implemented by allowing the surgeon to interactively manipulate a graphical cursor on the screen whereby he can specify the desired zoom factor by enlarging or contracting one such cursor with respect to a reference cursor whose size does not change during the zoom factor specification. Any appropriate input device 248 can be used to manipulate the cursor object. Computer 243 then uses the relative geometry of the two cursors to compute the direction and magnitude of the camera motion increment, which is necessary to effect the specified zoom factor. Alternatively, voice input can be used to specify the zoom factor. Once the camera motion increment has been computed, computer 243 instructs manipulator 242 to (slowly) reposition the camera tip 266 by that amount along the axis of view, thereby obtaining the desired zoom factor. Note that the point p, as defined above, remains at the center of the image throughout the zooming process.

In another mode, the surgeon can directly control a desired direction of motion of the camera vantage point via an instrument-mounted input device. In the preferred embodiment, this input device is a six degree-of-freedom joystick. Using such a joystick, the surgeon can then arbitrarily reposition and reorient the camera in all six degrees of freedom simultaneously. By selecting different subsets of the full six degree-of-freedom motion, a number of useful control modes can be implemented. In particular, if the translational controls of the six degree-of-freedom joystick are disabled or only a three degree-of-freedom input device is available, a camera motion control mode can be implemented, where the camera tip is constrained to move along the surface of an imaginary sphere, centered at the current anatomical feature of interest and having radius equal to the current distance of the camera tip from the feature. In another embodiment, where only a two degree-of-freedom input device is available, any two of the six degrees of freedom can be controlled by the device at any given time. For instance, pressing a two degree-of-freedom joystick in the direction toward the tip of the instrument on which the joystick is mounted can be interpreted to mean "zoom in", and pressing away from the tip can mean "zoom out". Releasing the joystick can mean "stop". Similarly, exerting pressure or force on a two degree-of-freedom joystick in a direction perpendicular to the long axis of the camera can be interpreted by computer 243 to mean a desired lateral motion of the camera at the current elevation in the direction of the exerted pressure. Additionally, the velocity of the camera motion can be made proportional to the amount of exerted pressure on the joystick.

In another mode the surgeon can manipulate a graphical object superimposed on the image of the patient's anatomy to specify a desired view of a particular feature of interest. The camera is then automatically positioned to achieve the desired view. A particular implementation of this mode would proceed as follows: An image of the patient's anatomy is obtained and displayed to the surgeon on a display monitor. The surgeon is then allowed to designate a feature of interest in a 2D or 3D image, unless the desired feature has already been designated and is visible. Next the surgeon can interactively manipulate a graphical object (e.g., cursor, slider, etc.) superimposed on the image of the patient's anatomy on the display screen to specify the desired view of the feature of interest. For example, the view specification could specify the desired vantage point of the camera anywhere on the surface of a sphere of a given radius centered at the feature of interest. Computer 243 then computes the appropriate displacement of the camera and instructs the manipulator 242 to execute the motion, thereby obtaining the desired view of the feature of interest.

If the surgical augmentation system comprises two independently controlled robotic systems, as illustrated in FIG. 4, another mode of using the 3D positional information about the patient's anatomical features to reposition a surgical instrument can be used, where the instrument being repositioned is the second surgical instrument, rather than the surgical telescope. In one embodiment of this invention, the second surgical instrument could be surgical forceps, which are repositioned such that the jaws of the instrument are coincident with the current 3D anatomical feature and a tissue sample of this feature can thus be obtained by closing the instrument's jaws.

Figure 10:
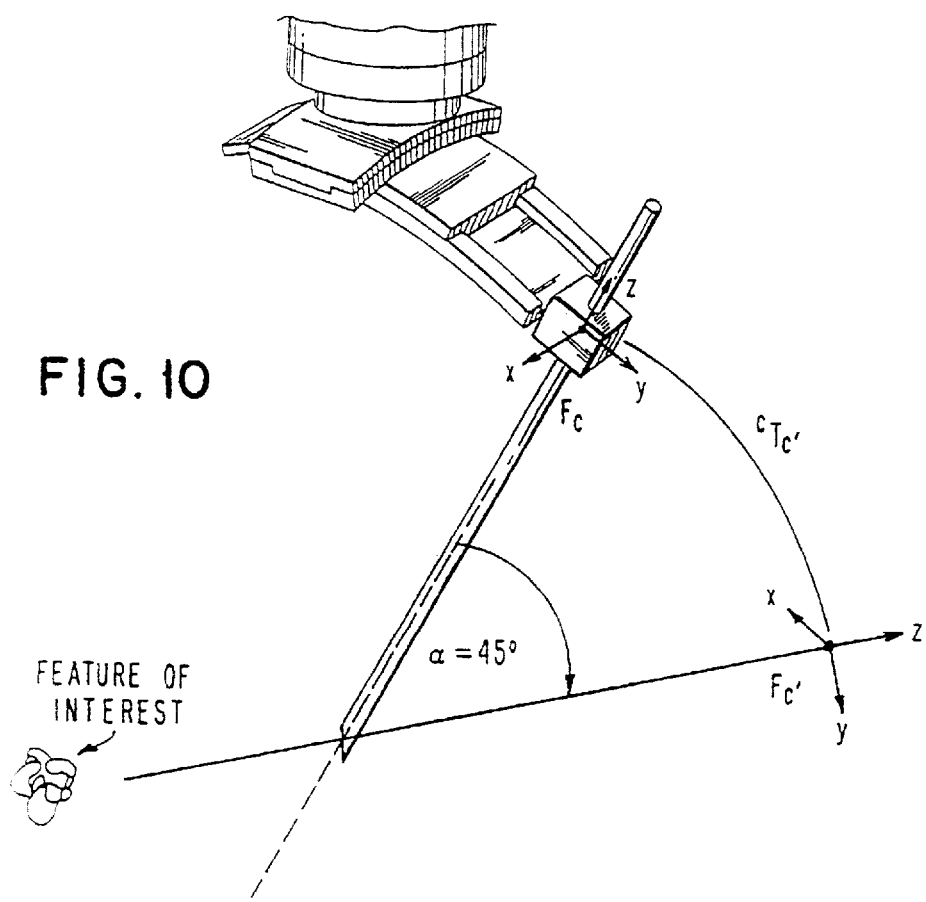
FIG. 10 shows a method of using oblique medical telescopes.

Referring to FIG. 10, the capability of interactively designating the desired view of a particular 3D feature of interest and letting the computer compute the resulting new location of the medical telescope is especially important in situations where the telescope's optics provide a lateral, rather than a straight-ahead ($(\alpha=0°)$ view. Telescopes with the direction-of-view anywhere between 30° and 135° (with respect to the instrument's long axis) are commonly used in laparoscopic and similar procedures. FIG. 10 illustrates a telescope with the direction-of-view of $\alpha=45°$. Manually positioning such a telescope to achieve a desired view can be extremely difficult even for an experienced camera operator as the relative transformations between the telescope, the patient's anatomy and the image coordinates become rather complex and unintuitive. However, adding a single rigid body transformation to the computational chain in the computer software accounts for the fact that the direction-of-view is different from 0°. In a particular implementation, a coordinate frame $F_c$, is associated with a 0° telescope, and the computer keeps track of the rigid body transformations between the manipulator, the camera, and the various anatomical features of interest. The mathematical methods and techniques of representing and manipulating rigid body transformations are well known to the art of robotics and computer graphics. Camera motions needed to effect a particular zoom factor, for example, are then computed relative to this camera frame $F_c$. For the case of a non-straight telescope, such as the telescope in FIG. 10, a new coordinate frame $F_d$ is defined by rotating the frame $F_c$, through an angle of $-\alpha$ about a line passing through the center of the lens tip and parallel to the X-axis of the coordinate frame $F_c$. The rigid body transformation $^cT_d$ relating the new camera frame $F_d$ to the default, 0° location of the camera frame $F_c$, is used to account for the non-zero direction of view of the telescope. Using the transform $F_d$ in place of $F_c$ in the computation of the new desired position of the telescope for a particular desired view now results in correct repositioning of the telescope regardless of its direction-of-view.

The visual information transmitted from the patient's body and optionally augmented by image processing and computer graphics can be displayed to a surgeon in a number of ways.

Referring to FIG. 1, in one mode of information display, the images of the patient's anatomy can be displayed to the surgeon as a combination of live and still images (a live image is an image obtained from the camera that is continuously updated with new information, whereas a still image is not). In one embodiment of this mode, the image to be displayed on the monoscopic monitor 247 is produced as follows: A wide-angle monoscopic image of the patient's anatomy is obtained using the surgical instrument 254 and displayed on the monitor 247 as a static image. The camera is then zoomed in for a closer view of the current feature of interest and a portion of this live TV image is displayed superimposed on top of the static wide-angle image. The static monoscopic view of the overall area of interest thus provides contextual information about the patient's anatomy under observation, whereas the live subimage shows a magnified detail area surrounding the current anatomical feature of interest.

In an alternative embodiment of this display modem, the static wide-angle contextual information can be a computer-graphic rendering of the patient's anatomy. This graphical information can be derived from computer models of the patient's anatomy constructed on the basis of the information gathered during preoperative imaging and scanning. As before, a portion of the image surrounding the current anatomical feature of interest is replaced with a live magnified TV image of this area. Here, the computer generated image and actual live TV image are merged into a single display image and must thus be properly registered with respect to each other to ensure proper correspondences of anatomical points and features between the two images. A number of techniques for achieving registration between images are known to the art. In the simplest embodiment, the 3D locations of a number of known anatomical landmarks represented in the computer model would be identified by 3D image processing techniques. The 3D locations of these landmarks can then be used to compute the appropriate perspective view for displaying the graphical model.

In another embodiment of this display mode, the static wide-angle contextual information can be a computer-graphic rendering of the patient's anatomy, as above. Similarly, a portion of the image surrounding the current anatomical feature of interest is replaced with a live magnified TV image of this area, as above. In addition, the live TV image of the area of detail can be augmented by superimposing static edge information, which can be derived either from a computer graphics model or as a result of image processing (edge extraction) on the TV image. The advantage of this display mode is that the superimposed edges highlight the ongoing changes within the area of detail reflected in the live TV image with respect to the previous (static) appearance of this area.

In another embodiment of this mode of displaying information to the surgeon, the static wide-angle view of the overall area of interest can be displayed as a static stereoscopic image. Referring to FIG. 1, this is achieved as follows: A static image of the overall area of interest is obtained from a first vantage point using the surgical instrument 254 and camera 259. The tip of the camera lens 266 is then displaced by a small known amount and a second static image of the area of interest is taken from this displaced vantage point. The two images are then fed as input to the stereo display system 271 and displayed on the steroscopic monitor 272 as a static stereoscopic wide-angle view of the overall anatomical area of interest. In some cases where only the distal manipulator 240 is moved to displace the camera, there may be some small angular misalignment of the two images so obtained. Experiment has shown that this misalignment can often be ignored, since the human visual system is very adept at fusing slightly misaligned images. Alternatively, the misalignment can be largely compensated for by using image transformation techniques known in the art. Next, the camera is zoomed in for a close-up view of the current anatomical feature of interest and a portion of the static wide-angle image is replaced by the magnified live monoscopic view of the anatomical feature of interest, as before. This results in an image, where the overall contextual information is a static stereoscopic image, providing the surgeon with a sense of the global three-dimensional relationships within the viewing volume, and the area surrounding the current anatomical feature of interest, where the surgeon's concentration is focused, is magnified and displayed as a live monoscopic image.

In a modification of the above mode of display, the live TV image of the area of detail can be augmented by superimposing static edge information, which can be derived either from a computer graphics model or as a result of image processing (edge extraction) on the TV image. As described previously, the advantage of this display mode is that the superimposed edges highlight the ongoing changes within the area of detail reflected in the live TV image with respect to the previous (static) appearance of this area.

Referring to FIG. 3, another embodiment of the present invention regarding display of visual information to the surgeon, uses the stereoscopic medical camera 254a to obtain a static stereoscopic wide-angle image of the overall anatomical area of interest. Then, as above, the stereoscopic camera is zoomed in closer over the current 3D anatomical feature of interest and a portion of the static image surrounding the feature of interest is replaced by a magnified live stereoscopic TV image as transmitted from the patient's body by cameras 259a and 259b.

In order to emphasize the changes occurring within the area of detail, edge information corresponding to a previous state of the area of detail can be superimposed on the live stereoscopic image, as before.

Again referring to FIG. 3, another embodiment of the present invention uses the stereoscopic medical camera 254a in conjunction with stereoscopic computer graphics to provide a display of the patient's anatomy. In this embodiment, the static stereoscopic view of the overall anatomical area of interest is derived from computer models of the patient's anatomy and displayed on the monitor 272 as a 3D stereoscopic graphical image via the stereo display system 271. As above, the stereoscopic camera is then zoomed in closer over the current 3D anatomical feature of interest and a portion of the static graphical image surrounding the feature of interest is replaced by a magnified live stereoscopic TV image as transmitted from the patient's body by cameras 259a and 259b.

Again, in order to emphasize the changes occurring within the area of detail, edge information corresponding to a previous state of the area of detail can be superimposed on the live stereoscopic image, as before.

Referring to FIG. 1, another mode of display of anatomical information to a surgeon uses the monoscopic camera 254 to provide the surgeon with a live stereoscopic image or the patient's anatomy. In this mode, the information supplied to one of the surgeon's eyes is derived from computer models of the patient's anatomy and is displayed as a graphical image computed from the vantage point displaced a small known distance laterally from the current vantage point of the surgical instrument 254. The information supplied to the other eye is the live image of the patient's anatomy as provided by the camera 259 attached to the surgical instrument 254. In this mode, one eye therefore receives static computer generated view of the patient's body, whereas the other eye receives a live image transmitted by the camera from a slightly displaced vantage point. If the computer-graphic model is properly registered with the actual anatomy, the human brain will fuse the two images into a proper 3D stereoscopic image.

In another embodiment of the above mode of display of anatomical information to the surgeon, image processing is used in conjunction with live video information to produce a live stereoscopic display to the surgeon. Referring to FIG. 1, in this embodiment of the present invention, a first image of the patient's anatomy under observation is obtained and transferred to the image processing system 245. The camera tip 266 is then displaced laterally a small known amount and a second image is obtained from this second vantage point and transferred to the image processing system 245. The image processing system and known image processing techniques are then used to extract edge information from the two images. A stereoscopic display is then produced by supplying the stereo display system 271 with only edge information in one of the input channels (left/right eye) and a live video signal with overlaid edge information in the other input channel (right/left eye). Subsequently, only information to one of the two eyes is updated with live video as transmitted by camera 259. This provides enough information for the human brain to "fill in" the missing information and interpret the image as a proper stereoscopic 3D image.

Alternatively, a display mode as above can be used, where the edge information is not obtained by image processing, but rather derived from a computer graphical model of the patient's anatomy.

Aside from visual information, the surgeon can receive non-visual information about the locations of features or the general state of the system as well. One non-visual channel of communication between the surgeon and the system is the voice recognition and speech synthesis subsystem (267, FIG 1). For example, synthesized voice messages can be issued by the system to inform the surgeon of the exact location of his surgical instrument with respect to an anatomical feature or interest. Likewise, synthesized messages confirming successful receipt of a voice command can be used to assure the surgeon that the system correctly interpreted his command (s). General system state or change of system state information can be relayed to the surgeon using synthesized voice as well. An example of this would be a synthesized speech message to the surgeon stating the exact distance by which the camera was moved during a zooming operation.

An alternative method of relaying non-visual information to the surgeon is tactile feedback. In one embodiment of this invention, tactile feedback conveyed to the surgeon through a hand-held or instrument-mounted input device (such as a joystick) can be used to alert the surgeon that he has positioned a graphical object or a surgical instrument in the vicinity of the current anatomical feature of interest. The tactile feedback can be delivered to the surgeon's hand or finger (whichever is in contact with the joystick) by instrumenting the joystick control with a computer controlled vibrator. When the vibrator is activated by the computer, the joystick control starts vibrating with appropriate frequency and amplitude, such that the oscillations are readily discernible by the surgeon, but do not distract him from his positioning task or otherwise interfere with his work.

We claim:

1. A surgical robotic system for use in minimally invasive surgery, the minimally invasive surgery performed at an internal surgical site of a patient body, the surgical robotic system comprising:
    a surgical instrument having a proximal end and a distal end, the instrument extendible distally through an incision to the internal surgical site;
    a robot supporting the proximal end of the instrument, the robot moving the instrument in response to motor signals;
    a voice recognition system for inputting spoken instructions; and
    a computer coupling the voice recognition system to the robot, the computer generating the motor signals in response to the spoken instructions to move the distal end of the surgical instrument at the internal surgical site by pivoting the instrument about the incision.

2. The surgical robotic system of claim 1, wherein the surgical instrument comprises an endoscope, and further comprising a monitor coupled to the endoscope for displaying an image of the internal surgical site.

3. The surgical robotic system of claim 2, wherein the distal end of the surgical instrument comprises a camera tip defining a camera coordinate frame, and wherein the computer calculates transformations between the camera coordinate frame and coordinate frames of the robot.

4. The surgical robotic system of claim 3, wherein the computer generates the motor signals using the transformations so that the camera tip moves in the internal surgical site to effect an instructed change in the image shown in the display.

5. The surgical robotic system of claim 3, wherein the camera tip defines a tip angle, and wherein the computer generates the motor signals using the transformations so that the camera tip moves in the internal surgical site to effect a change in zoom of the image shown in the display in response to a change in zoom instruction.

6. The surgical robotic system of claim 1, wherein the first surgical instrument is any of the following:
    a surgical tool;
    a forceps;
    a device positioned within the patient's body for transmitting an image outside of the patient's body;
    a laparoscope; and
    a medical telescope.

7. A minimally invasive surgical robotic method comprising:
    inserting a distal end of a surgical instrument through an incision to an internal surgical site;
    manipulating a proximal end of the instrument with a robot in response to motor signals;
    inputting spoken instructions into a voice recognition system;
    generating the motor signals in response to the spoken instructions with a computer; and
    moving the distal end of the surgical instrument at the internal surgical site by pivoting the instrument about the incision with the robot in response to the motor signals.

8. The surgical robotic method of claim 7, further comprising displaying an image of the internal surgical site on a monitor.

9. The surgical robotic method of claim 8, wherein the surgical instrument comprises an endoscope, and further comprising inputting a change of image instruction and moving the endoscope with the robot so as to effect the instructed image change.

10. The surgical robotic method of claim 9, wherein the instructed image change comprises a change in zoom.

11. The surgical robotic method of claim 10, wherein the endoscope has a camera tip disposed at an angle relative to a shaft of the camera.

12. The surgical robotic method of claim 7, wherein the distal end of the surgical instrument defines a distal coordinate reference frame, and further comprising calculating transformations between the distal coordinate frame and a coordinate frame of the robot with the computer and using the transformation to generate the motor signals.

13. A system for positioning a surgical instrument relative to a patient's body, comprising:
    a robotic manipulator having at least one controlled degree of freedom;
    a controller controlling the robotic manipulator;
    an instrument holder attaching a first surgical instrument to the robotic manipulator so that the first surgical instrument can pivot about an aperture into the patient body; and
    a voice recognition system coupled to the controller, the voice recognition system permitting a surgeon to verbally command motions of the robotic manipulator, the instrument pivoting about the aperture in response to the commands.

14. A system for positioning a surgical instrument relative to a patient's body, as in claim 13, wherein the voice recognition system further permits the surgeon to select commands or operating modes from menus.

15. A system for positioning a surgical instrument relative to a patient's body, as in claim 13, further comprising a speech synthesis system to provide the surgeon with voice messages containing information about the operation of the system.

16. A system for positioning a surgical instrument relative to a patient's body, as in claim 15, wherein the first surgical instrument is a surgical camera and the speech synthesis system provides a message to the surgeon stating information about the movement of the surgical camera.

17. A system for positioning a surgical instrument relative to a patient's body, as in claim 15, wherein the first surgical instrument is a surgical camera and the speech synthesis system provides a message to the surgeon stating information about the movement of the surgical camera effect a zoom operation of the surgical camera.

18. A surgical robotic system for use in minimally invasive surgery performed at an internal surgical site of a patient body, the system comprising:

a surgical instrument having a proximal portion and a distal end, said instrument extendable distally through an aperture in a body wall to the internal surgical site;

a robotic arm supporting the proximal portion of the instrument, the robotic arm moving the instrument in response to motor signals;

a voice recognition system for inputting spoken instructions; and a computer operatively coupling the voice recognition system to the robotic arm, the computer generating the motor signals in response to the spoken instructions to move the distal end of the surgical instrument at the internal surgical site while the surgical instrument pivots about the aperture.

19. The surgical robotic system of claim 18, wherein the surgical instrument comprises an endoscope, said system further comprising a display operatively coupled to said endoscope for allowing a surgeon to view an image of the internal surgical site.

20. The surgical robotic system of claim 19, wherein the computer generates said motor signals so that the endoscope distal end moves at the internal surgical site to effect an instructed change in the image shown in the display.

21. The surgical robotic system of claim 19, wherein the computer generates said motor signals so that the endoscope distal end moves at the internal surgical site to effects an instructed change in zoom of the image shown in the display in response to a change in zoom instruction.

22. The surgical robotic system of any of claims 18–21, wherein the voice recognition system comprises a microphone for detecting spoken instructions and a speaker for providing audible messages to a surgeon regarding operation of the system.

23. The system of claim 22, wherein said audible messages comprise audible feedback indicating successful receipt of said spoken instructions.

24. The system of claim 22, wherein said audible messages comprise synthesized voice messages.

25. The system of claim 22, wherein said audible messages comprise audible feedback indicating undesired movement of the distal end of the surgical instrument.

26. A minimally invasive surgical robotic method comprising:

inserting a distal end of a surgical instrument through an aperture in a body wall of a patient to an internal surgical site;

manipulating a proximal portion of said instrument with a robotic arm in response to motor signals;

inputting spoken instructions into a voice recognition system;

generating, with a computer, said motor signals in response to said spoken instructions; and moving the robotic arm in response to the motor signals so as to move the distal end of the surgical instrument at the internal surgical site.

27. The method of claim 26, wherein said surgical instrument comprises an endoscope, the method further comprising displaying an image of the internal surgical site for perception by a surgeon.

28. The method of claim 27, further comprising inputting a change of image instruction and moving the endoscope with the robotic arm so as to effect the instructed image change.

29. The method of claim 28, wherein the instructed image change comprises a change in zoom.

30. The method of any of claims 26–29, further comprising providing audible messages containing information about the robotic surgery.

31. The method of claim 30, wherein said audible messages comprise audible feedback indicating successful receipt of said spoken instructions.

32. The method of claim 30, wherein said audible messages comprise synthesized voice messages.

33. The method of claim 30, wherein said audible messages comprise audible feedback indicating undesired movement of the distal end of the surgical instrument.

34. A system for positioning an endoscopic surgical instrument relative to a surgical site within a patient's body, comprising:

a robotic manipulator having at least one controlled degree of freedom;

a controller that is adapted to be capable of controlling the robotic manipulator;

an instrument holder for coupling said surgical instrument to said robotic manipulator; and a voice recognition command input system operatively coupled to the controller, the voice recognition system permitting a surgeon to specify desired motion of the surgical instrument to the controller, such that the robotic manipulator moves said instrument to a position relative to the patient's body, as specified by the surgeon using the command input system, by pivoting the instrument about an aperture into the patient's body.

35. A surgical robotic system for use in minimally invasive surgery performed at an internal surgical site of a patient body, the system comprising:

a surgical instrument having a proximal portion and a distal end, said instrument extendable distally through an aperture in a body wall to the internal surgical site;

a robotic arm supporting the proximal portion of the instrument, the robotic arm moving the instrument in response to motor signals;

a computer operatively coupling the robotic arm to a surgeon input device, the computer generating the motor signals in response to a surgeon's input to move the distal end of the surgical instrument at the internal surgical site within the patient body; and a voice synthesis system for providing audible information to a surgeon regarding operation of the system during the surgery.

36. The surgical robotic system of claim 35, wherein the surgical instrument comprises an endoscope, said system further comprising a display operatively coupled to said endoscope for allowing a surgeon to view an image of the internal surgical site.

37. The surgical robotic system of claim 36, wherein the computer generates said motor signals so that the endoscope distal end moves at the internal surgical site to effect an instructed change in zoom of the image shown in the display in response to a change in zoom instruction.

38. The surgical robotic system of any of claims 35–37, wherein the input device comprises a voice recognition system comprising a microphone for detecting spoken input instructions.

39. The surgical robotic system of claim 36, wherein the computer generates said motor signals so that the endoscope distal end moves at the internal surgical site to effect an instructed change in the image shown in the display.

40. The system of claim 35, wherein said audible information comprises information concerning the degree of movement of the distal end of said instrument in response to the surgeon's most recent input command.

41. The system of claim 35, wherein said audible information comprises information concerning a location of the distal end of said instrument with respect to an anatomical feature of interest.

42. The system of claim 35, wherein said audible information comprises information indicating undesired movement of the distal end of the surgical instrument.

43. An apparatus for moving a surgical instrument, comprising:

a robotic arm assembly coupled to said surgical instrument;

an input device that receives an input voice command and communicates a corresponding signal to a computer, said input voice command indicating a desired movement of said instrument, said computer providing a movement command, corresponding to said signals to move said assembly so that said surgical instrument is moved according to said desired movement by pivoting the surgical instrument at an aperture.

44. An apparatus for moving a surgical instrument, as in claim 43, wherein a voice recognition system further permits the surgeon to select commands or operating modes from menus.

45. An apparatus for moving a surgical instrument as in claim 43, wherein a speech synthesis system provides the surgeon with voice messages containing information about the operation of the system.

46. An apparatus for moving a surgical instrument, as in claim 43, wherein the surgical instrument is a surgical camera and a speech synthesis system provides a message to the surgeon stating information about the movement of the surgical camera.

47. An apparatus for moving a surgical instrument, as in claim 45, wherein the surgical instrument is a surgical camera and a speech synthesis system provides a message to the surgeon stating information about the movement of the surgical camera to effect a zoom operation of the surgical camera.

48. An apparatus for moving a surgical instrument as in claim 43, wherein the surgical instrument comprises any one of the following:

a surgical tool;

a forceps;

a device positioned within the patient's body for transmitting an image outside of the patient's body;

a laparoscope; and a medical telescope.

49. The system of claim 43, wherein said computer, after receiving said signal, compares said signal with at least one predetermined command signal and verifies that said input voice command is acceptable.

50. The system of claim 43, further comprising an audio device for providing a user with a message confirming receipt of the input voice command.

* * * * *

Disclaimers 6,201,984—Janez Funda, Valhalla; David Aruthur LaRose, Croton on Hudson; Russell Highsmith Taylor, Ossining, all of NY. SYSTEM AND METHOD FOR AUGMENTATION OF ENDOSCOPIC SURGERY. Patent dated March 13, 2001. Disclaimer filed March 11, 2002, by the assignee, IBM Corporation.

Hereby disclaims and dedicate to the public all claims (1-50).

*(Official Gazette, July 2, 2002)*